US00PP31609P2

(12) United States Plant Patent
Geoghegan

(10) Patent No.: US PP31,609 P2
(45) Date of Patent: Mar. 31, 2020

(54) STRAWBERRY PLANT NAMED 'LADY ISABELLA'

(50) Latin Name: ***Fragaria* x *ananassa* (Duch.)**
Varietal Denomination: Lady Isabella

(71) Applicant: S&A Soft Fruits Ltd., Marden, Herefordshire (GB)

(72) Inventor: Irene Geoghegan, Dundee (GB)

(73) Assignee: S&A Soft Fruits Ltd., Marden (GB)

( * ) Notice: Subject to any disclaimer, the term of this patent is extended or adjusted under 35 U.S.C. 154(b) by 0 days.

(21) Appl. No.: 16/501,833

(22) Filed: Jun. 13, 2019

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208
CPC ..... A01H 5/08; A01H 6/74
See application file for complete search history.

*Primary Examiner* — Annette H Para
(74) *Attorney, Agent, or Firm* — The Webb Law Firm

(57) ABSTRACT

A new and distinct strawberry plant is provided having early ripening, sweet tasting, and attractively shaped fruits.

4 Drawing Sheets

Botanical classification: *Fragaria* x *ananassa* (Duch.).
Varietal denomination: 'Lady Isabella'.

BACKGROUND OF THE INVENTION

The present invention comprises a new and distinct variety of strawberry plant botanically classified as *Fragaria* x *ananassa* (Duch.) and known by the varietal name 'Lady Isabella'. The new variety was originally referred to as RD072-004-2012. The new variety is the result of a cross between strawberry seedling referred to as SA40 (female parent, unpatented) and strawberry seedling referred to as SA23 (male parent, unpatented). The resultant cross produced 'Lady Isabella' in July of 2013 in Herefordshire, United Kingdom. The purpose of the breeding program was to develop novel everbearing and day neutral strawberry varieties. Subsequently, the new variety was asexually reproduced via stolons in Herefordshire, United Kingdom in August of 2013. The new variety has been trial and field tested and has been found to retain its distinctive characteristics and remain true to type through successive asexual propagations. The new variety has not been evaluated under all possible environmental conditions. The phenotype may vary with variations in environment without a change in the genotype of the plant.

The new variety is similar to its female parent in its remontant behavior (daughter plants flower), attractive conic to cordate-shaped fruit, and open plant growth habit. However, the calyx of 'Lady Isabella' tends to invert when a berry is fully ripe, while the calyx of its female parent remains closed around the berry. Further, 'Lady Isabella' exhibits larger flowers and fruit than its female parent. The new variety is similar to its male parent in having berries with a consistently high Brix level and a glossy finish to the berry skin. However, 'Lady Isabella' differs from its male parent in providing fewer berries per truss (3-5 for 'Lady Isabella' versus 6-8 for its male parent) and exhibiting a more rounded berry shoulder than its male parent.

When compared to strawberry variety named 'Lady Emma' (U.S. Plant patent application Ser. No. 16/501,678, filed May 21, 2019), 'Lady Emma' exhibits a stronger remontant flowering behavior, a more compact growth habit, a shorter canopy, and greater fruit yields. Further, the fruit of 'Lady Isabella' transitions from a mottled pink to a deep red color, while the fruit of 'Lady Emma' is paler and more orange-colored than that of 'Lady Isabella'.

The following characteristics also distinguish the new variety from other strawberry varieties known to the breeder:

- Consistently high Brix content;
- Early ripening and everbearing fruit;
- Mottled pink fruit coloration before reaching full ripeness;
- Calyx inversion of fully ripened fruit;
- Strongly concaved/cupped mature leaves; and
- Plump shouldered fruit that provides for a slightly reniform/cordate appearance.

DESCRIPTION OF THE DRAWINGS

The accompanying photographic drawings illustrate the new variety at approximately 10 months of age, with the color being as nearly true as is possible with color illustrations of this type. It should be noted that colors may vary with growing conditions and time of year.

DESCRIPTION OF THE PLANT

Figure 1:
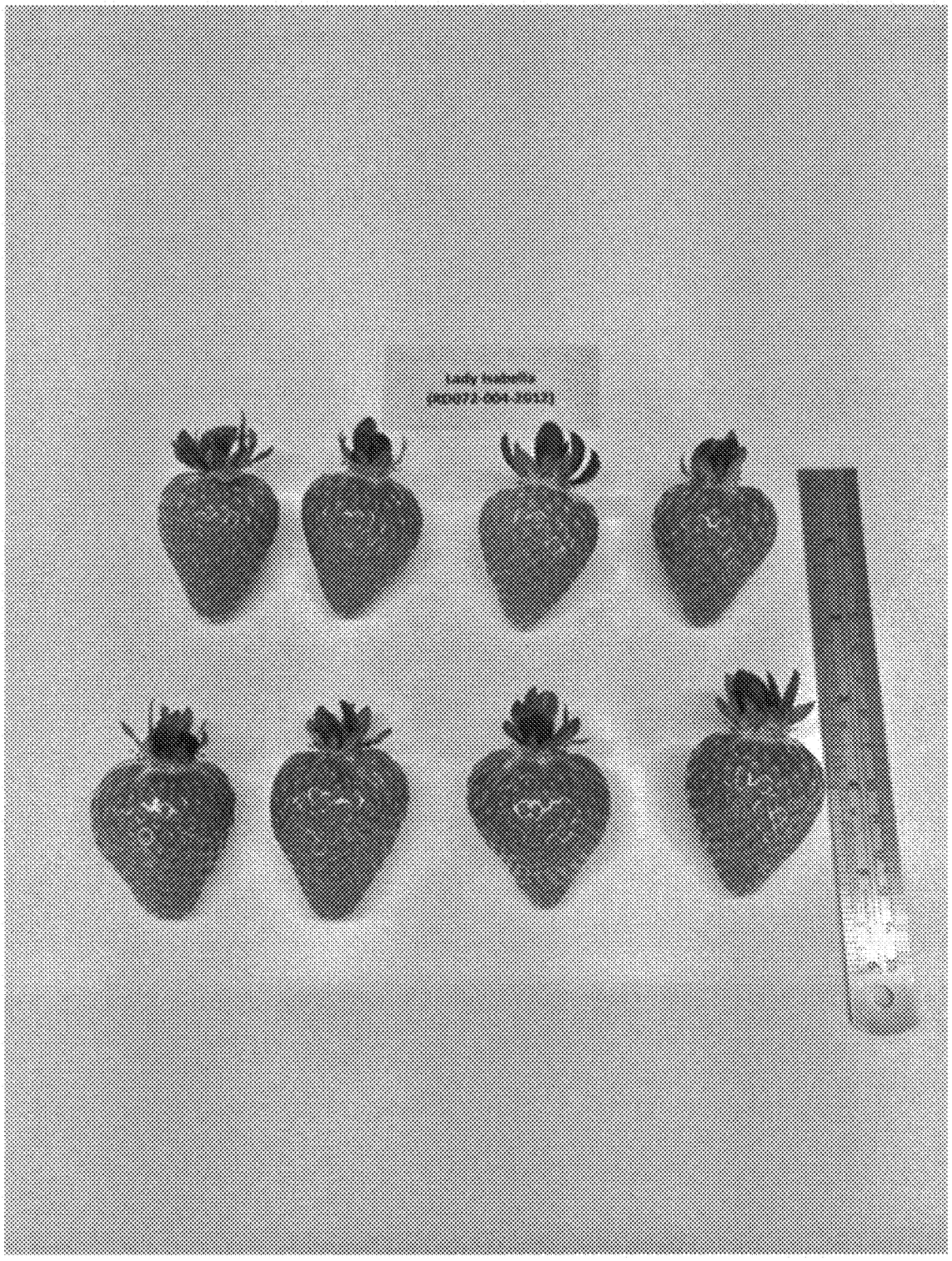
FIG. 1 is a photograph of multiple fruits of the new variety.
Figure 2:
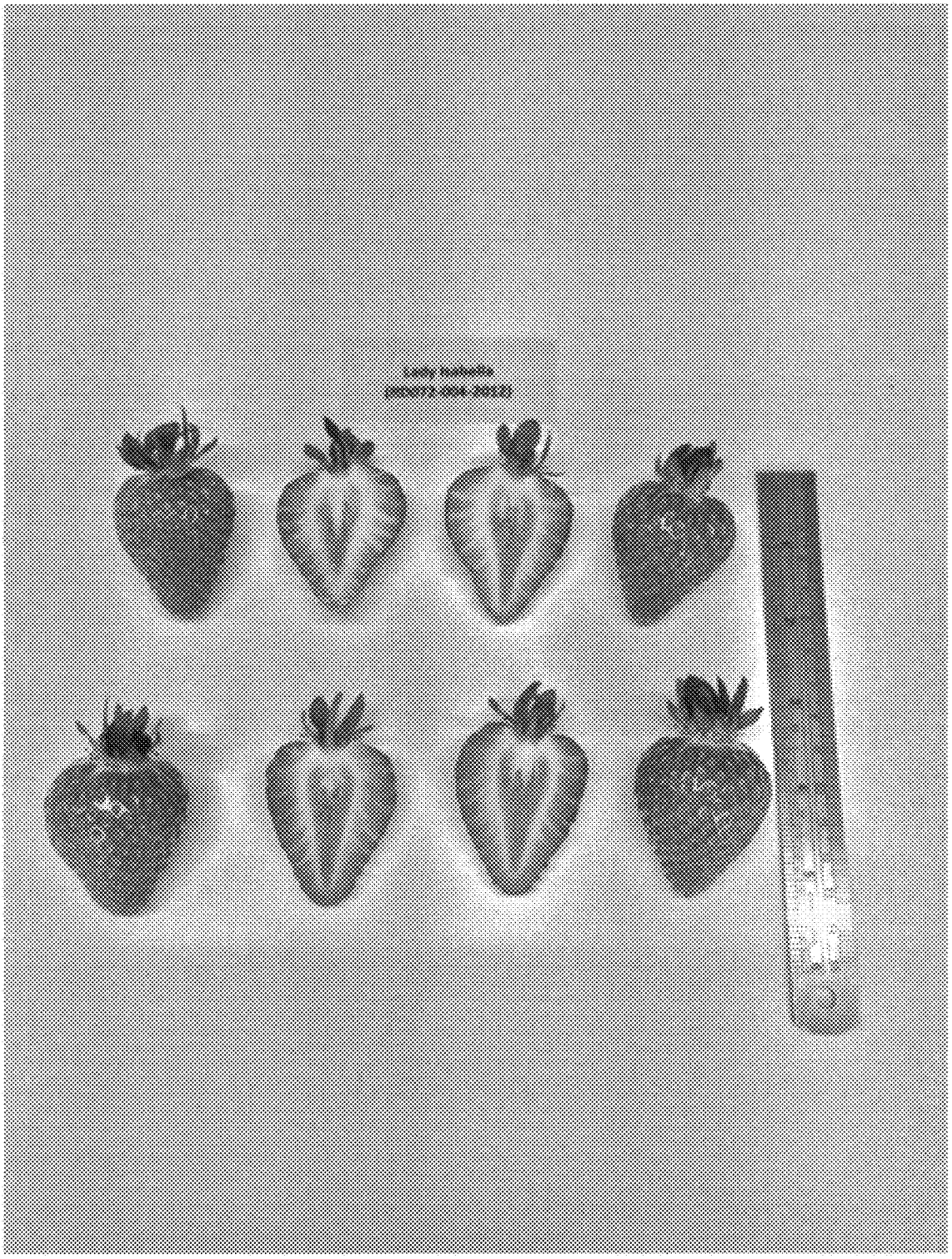
FIG. 2 is a photograph of whole and halved fruits of the new variety.
Figure 3:
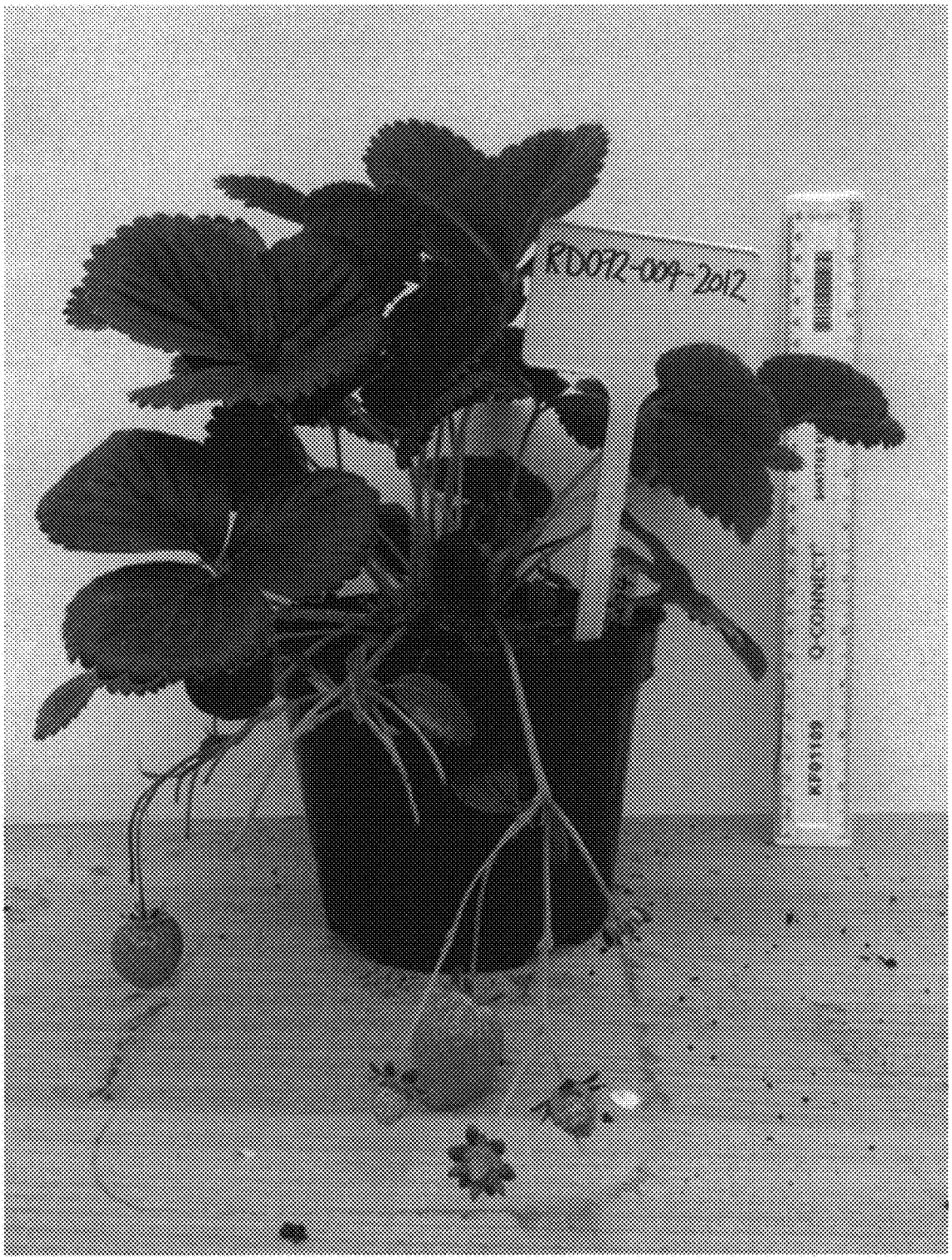
FIG. 3 is a photograph of an entire plant of the new variety.
Figure 4:
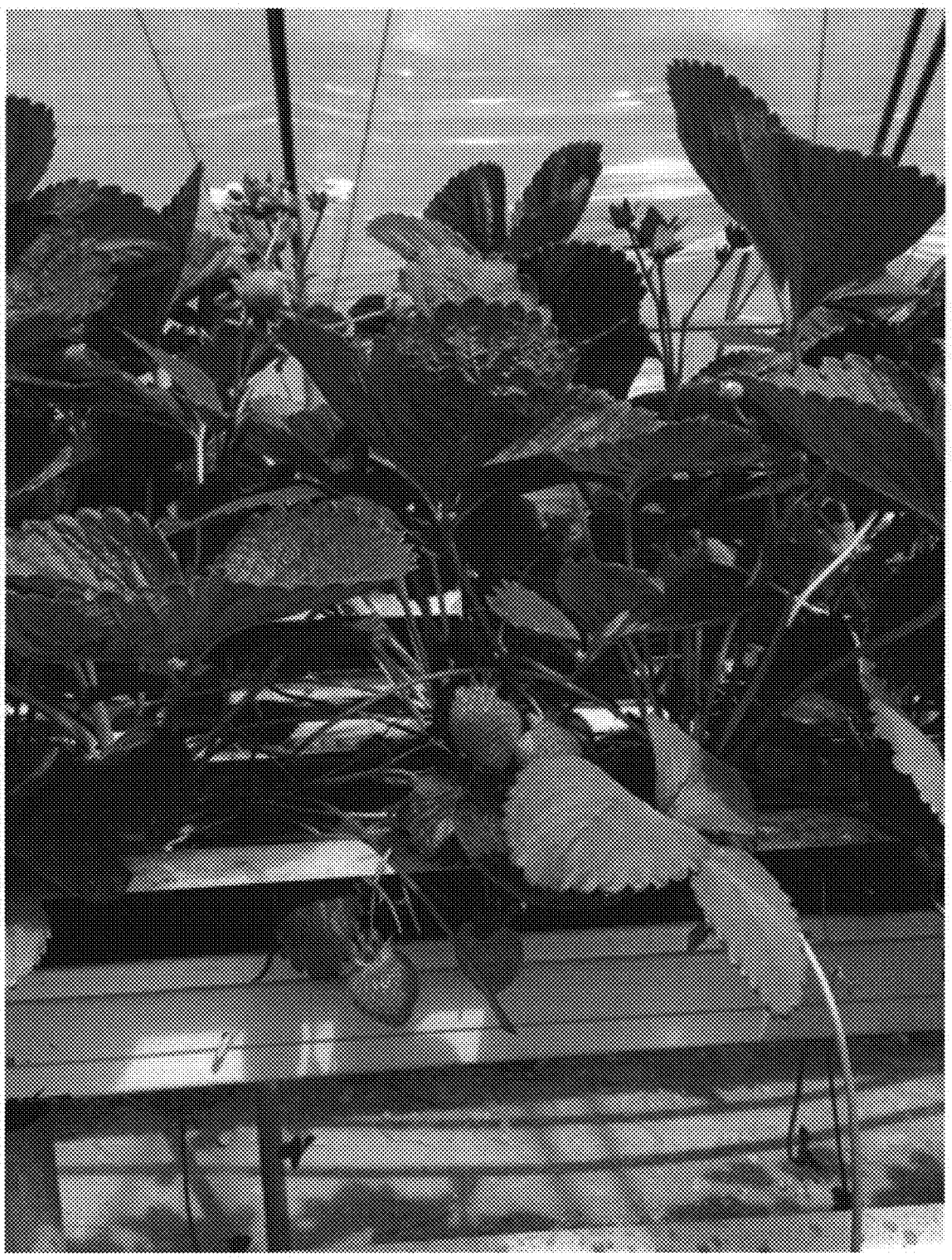
FIG. 4 is a photograph of multiple plants of the new variety.

The following detailed description sets forth the characteristics of the new cultivar. The new variety was grown under polytunnel protection in 2 liter containers in Herefordshire, United Kingdom with heat provided to provide an average day temperature of 16° C. The new variety was approximately 10 months of age when described. Color references are primarily to the Sixth Edition (2015) of The R.H.S. Colour Chart of The Royal Horticultural Society of London and were identified under natural light.

PLANT

Time to initiate roots: 48-72 hours at an average temperature of 20° C.

Time to produce a rooted plant: 30-35 days at an average temperature of 20° C.

Rooting habit: Reasonably vigorous.

Plant form: Open and spreading.

Height (from soil to top of plant): 35-40 cm.

Plant diameter: 50-65 cm.

Vigor: Moderate.

Disease/pest resistance: Strongly resistant to powdery mildew.

Weather tolerance: Plants perform best in a protected environment.

Foliage:

*Arrangement*.—Basal rosette; upwardly facing.

*Number of leaves per stem*.—Generally three.

*Whole leaf length*.—15-30 cm.

*Whole leaf width*.—15-25 cm.

Petiole:

*Length*.—25-33 cm.

*Diameter*.—3.4-4.1 mm.

*Color*.—RHS 145A.

*Texture*.—Pubescence laterally facing.

Stipule:

*Average number per leaf*.—Usually 2-3.

*Length*.—2-3 cm.

*Width*.—5-8 mm.

*Color*.—Very weak pigmentation that is close to RHS 145B.

Color:

*Young leaflets*.—Upper surface: Close to RHS 146A. Lower surface: RHS 146B.

*Mature leaflets*.—Upper surface: RHS NN137A. Lower surface: RHS 147B.

Lateral leaflets:

*Length*.—8-13 cm.

*Width*.—6-12 cm.

*Shape of leaf* (*generally*).—Orbicular to obovate, basally asymmetrical, cross-sectionally concave.

*Shape of apex*.—Typically obtuse.

*Shape of base*.—Between acute and obtuse, basally asymmetrical,.

*Texture* (*both surfaces*).—Light covering of thin pubescence present.

*Aspect*.—Upright.

*Margin type*.—Crenate.

Terminal leaflets:

*Length*.—8-13 cm.

*Width*.—5.7-10.1 cm.

*Shape of leaf* (*generally*).—Orbicular, basally asymmetrical, cross-sectionally concave.

*Shape of apex*.—Rounded.

*Shape of base*.—Acute.

*Texture* (*both surfaces*).—Light covering of pubescence present.

*Aspect*.—Upright.

*Margin type*.—Crenate.

Veins:

*Venation pattern*.—Pinnate.

*Color*.—Upper surface: Close to RHS 144A. Lower surface: RHS 145C.

Fruit:

*Harvest season*.—From April-October in Herefordshire, United Kingdom.

*Number of fruit per fruiting lateral*.—Generally 3-5.

*Color*.—Immature: RHS 150D. Maturing: RHS 40C. Fully mature: RHS 44A. Evenness of color: Mottled and uneven when ripening, but generally even once ripe.

*Taste*.—Very good and sweet.

*Length*.—3.2-5.0 cm.

*Width*.—2.4-4.0 cm.

*Length/width ratio*.—Longer than wide.

*Overall shape*.—Conic to cordate.

*Glossiness*.—Strong.

*Weight*.—Typically from 17-22 g.

*Achene position*.—Slightly beneath surface level.

*Achene color*.—Generally close to RHS 1A.

*Average number of achenes per berry*.—227.

*Flesh firmness*.—Firm.

*Fruiting truss length*.—25-35 cm.

*Fruiting truss width*.—15-25 cm.

*Fruiting truss color*.—RHS 144B.

Reproductive organs:

*Stamens*.—Number per flower: 21-28. Length: 2.7-3.7 mm. Width: 1.0-1.5 mm.

*Anthers:*.—Apex shape: Rounded. Base Shape: Cordate. Length: 1.6-1.9 mm. Width: 1.0-1.4 mm. Color: Edge: Close to RHS 20A. Center: RHS 7A.

*Stigma*.—Texture: Lightly papillose. Shape: Rounded to ovate. Color: Close to RHS 6A.

*Style*.—Length: About 1.6 mm. Color: RHS 4A.

*Ovary*.—Texture: Pubescence present. Length: About 0.5 mm. Color: With seed: RHS 150C. Without seed: Close to RHS 150B.

*Stolon*.—Length: Mother plant to first stolon-plant: Approximately 70 cm. Mother plant to second stolon-plant: Approximately 120 cm. Diameter: 3.8 mm. Color: RHS 144C.

Flowers:

*Natural flowering season*.—From April-October in Herefordshire, United Kingdom.

*Number of flowers per plant*.—10-20.

*Fragrance*.—None present.

*Longevity*.—1 week before petal fall.

*Flower description*.—Rotate flowers arranged singly at lateral apices that are slightly concave with a strong overlap of neighboring petals.

*Flower height*.—7-13 mm.

*Flower diameter*.—22-27 mm.

*Petals*.—Number per flower: 5-7. Shape: Orbicular to obovate at base, petals are typically cross-sectionally concave. Length: Approximately 14 mm. Width: Approximately 13 mm. Apex: Rounded obtuse. Base: Acute. Margin: Entire. Texture (both surfaces): Smooth, with no pubescence present. Color: Mature petal: Upper surface: Close to RHS 155C. Lower surface: RHS 155C. Young petal: Upper surface: Close to RHS NN155C. Lower surface: Close to RHS NN155C.

*Sepals*.—Number per flower: 10-14. Length: 6-7 mm. Width: 4-5 mm. Shape: Lanceolate with a single point. Number: 10-14. Apex: Acute. Margin: Entire. Texture: Pubescence present on both upper and lower surfaces. Color: Mature sepal: Upper surface: Varies concentrically from flower center between RHS 139D (inner edge) to RHS 143A (outer edge). Lower surface: Close to RHS 137C. Young sepal: Upper surface: Close to RHS 143B. Lower surface: RHS 143B.

*Buds*.—Length: 7-10 mm. Diameter: 7.2-8.4 mm. Shape: Longer than wider. Color: RHS 145A.

I claim:

1. A new and distinct variety of strawberry plant, as is herein illustrated and described.

* * * * *